United States Patent
Hazart (10) Patent No.: US 7,307,723 B2
(45) Date of Patent: Dec. 11, 2007

(54) METHOD FOR THE OPTICAL CHARACTERIZATION OF MATERIALS WITHOUT USING A PHYSICAL MODEL

(75) Inventor: Jerome Hazart, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 114 days.

(21) Appl. No.: 10/540,003

(22) PCT Filed: Dec. 24, 2003

(86) PCT No.: PCT/FR03/50211

§ 371 (c)(1),
(2), (4) Date: Jun. 21, 2005

(87) PCT Pub. No.: WO2004/061432

PCT Pub. Date: Jul. 22, 2004

(65) Prior Publication Data

US 2006/0077386 A1 Apr. 13, 2006

(30) Foreign Application Priority Data

Dec. 30, 2002 (FR) .................. 02 16847
Oct. 2, 2003 (FR) .................. 03 50635

(51) Int. Cl.
*G01J 4/00* (2006.01)
(52) U.S. Cl. .................. 356/369
(58) Field of Classification Search .................. None
See application file for complete search history.

(56) References Cited

U.S. PATENT DOCUMENTS 5,416,338 A * 5/1995 Suzuki et al. .................. 257/21
5,682,402 A * 10/1997 Nakayama et al. .................. 372/99
5,956,145 A 9/1999 Green et al.
6,614,823 B2 * 9/2003 Funabashi et al. .................. 372/50.11
2006/0077386 A1 4/2006 Hazart

FOREIGN PATENT DOCUMENTS

WO 02/27288 4/2002

OTHER PUBLICATIONS

D. Bhattacharyya et al.: "Spectroscopic ellipsometry of multilayer dielectric coatings", Vacuum, vol. 60, No. 4, pp. 419-424, Mar. 2001. XP-002954104.

Jean Garrigues: "La methode des elements finis", 'Online!, pp. 1-83, Jan. 2002. XP-002254500.

(Continued)

*Primary Examiner*—Tu T. Nguyen
(74) *Attorney, Agent, or Firm*—Oblon, Spivak, McClelland, Maier & Neustadt, P.C.

(57) ABSTRACT

A method of optical characterization of a layer of material in which the spectrum of index $n^*$ ($\lambda$) is characterized by a limited number of "nodes" that are points with coordinates ($\lambda_i$, $n_i$, $k_i$) or ($\lambda_i$, $n^*_i$), with $n_i = n(\lambda_i)$, $k_i = k(\lambda_i)$ and $n^*_i = n_i + jk_i$, where $j^2 = -1$, and an interpolation law between the "nodes," which can be, for example, linear, cubic, of "spline" type or polynomial (of any given degree). This interpolation law allows the calculation, from the "nodes," of the refraction indexes and the extinction coefficients for the wavelengths located between the "nodes."

21 Claims, 3 Drawing Sheets

OTHER PUBLICATIONS

Babar K. Minhas et al.: "Ellipsometric scatterometry for the metrology of sub-0.1-μm-linewidth structures", Applied Optics, vol. 37, No. 22, pp. 5112-5115, Aug. 1, 1998. XP-001162836.

Fred L. Terry, Jr.: "A modified harmonic oscillator approximation scheme for the dielectric constants of AlxGa1-xAs", Journal of Applied Physics, vol. 70, No. 1, pp. 409-417, Jul. 1, 1991.

R.M.A. Azzam and N.M. Bashara: "Ellipsometry and Polarized Light", Chapter 6, pp. 417-486, no date.

Max Wolf Born: "Principles of Optics", 7th, exp. ed. 1999.

A. R. Forouhi: "Optical dispersion relations for amorphous semiconductors and amorphous dielectrics", Physical Review B, vol. 34, No. 10, pp. 7018-7026, Nov. 15, 1986.

W. H. Press, S. A. Teukolsky, W. T. Vetterling, B. P. Flannery: "Numerical Recipes in C: The Art of Scientific Computing", $2^{nd}$ Edition, Chapter 3, pp. 105-123, no date.

W. H. Press, S. A. Teukolsky, W. T. Vetterling, B. P. Flannery: "Numerical Recipes in C: The Art of Scientific Computing", 2nd Edition, Chapter 10, pp. 394-455, no date.

"High Precision UV-Visible-Near IR Stokes Vector Spectroscopy," Zettle et al.; Thin Solid Films, 234 (1993).

"Ellipsometry on Very Thick Multilayer Structures" Garriga et al., Phys. Stat. Sol. (b) 215, 247 (1999).

"Temperature Deopendence of the lnP(001) Bulk and Surface Dielectric Function" Zom et al.; App. Phys. A, 65, 333-339 (1997).

\* cited by examiner

METHOD FOR THE OPTICAL CHARACTERIZATION OF MATERIALS WITHOUT USING A PHYSICAL MODEL

TECHNICAL FIELD

The invention relates to a method of optical characterisation of materials.

This method allows to characterise thin or thick layers of these materials, which are created on substrates. The physical dimensions, that this method allows to determine, are:
- the thickness of a layer of material;
- the refraction index of this material; and
- the absorption coefficient of this material.

Optical characterisation of materials is used for the chemical analysis of these materials (notably the study of absorption bands, of densification properties and of oxidation properties), in the fields of microelectronics, sensors, biology, medicine, or to analyse the thickness of deposits of these materials.

We refer to document [1] for examples of applications which, as for the other documents cited later on, is mentioned at the end of this description.

The characterisation of the optical properties of a material is also useful when the material is structured later on (to create for example etchings or surface roughness) and the optical diffraction properties of the obtained structure must be calculated (see document [2]).

It can already be noted that the invention is particularly useful when the physical law applied by the complex refraction index of the material to be characterised is, a priori, unknown.

STATE OF THE PRIOR ART

Remember that the optical measurements can have a variety of natures.

It can be reflectometric measurements. In this case, the intensity reflection coefficient of a structure is measured over a spectrum (i.e. an interval) of wavelengths $[\lambda_m, \lambda_M]$.

The incident angle of the illuminating light may be not zero. The reflection coefficient can be measured for several incidence angles $\theta$. Let R ($\theta$, $\lambda$, p) be the reflectometric spectrum, where p is the polarisation of the incident beam and $\lambda$ the wavelength of the latter.

Generally, the angle $\theta$ is zero and the polarisation p unknown. In the event where $\theta$ is not zero, this polarisation p must be known. Generally, the latter is of (S) or (P) type.

It can also be ellipsometric measurements. The measured dimensions are then the real and imaginary parts of the ratio between the polarisation reflection coefficient (P) and the polarisation reflection coefficient (S).

We generally mark $\rho=|\rho|\exp(j\Delta)$ this complex ratio (with $j^2=-1$). The dimensions commonly handled are $|\rho|$, that we mark $\tan(\Psi)$, and $\cos(\Delta)$, or combinations of both.

For example, the variables derived from a phase modulation ellipsometer are the following:

$$I_s=\sin(2\Psi)\sin(\Delta) \text{ and } I_c=\cos(2\Psi).$$

As for a standard ellipsometer, it supplies the following variables:

$$\alpha=(\tan^2\Psi-1)/(\tan^2\Psi+1) \text{ and } \beta=\cos\Delta(1-\alpha^2)^{1/2}.$$

For generality purposes, we mark the handled dimensions $S_1$ and $S_2$.

The spectrums $S_i$, i$\in$ [1,2], are measured over a range of wavelengths $[\lambda_m, \lambda_M]$. The incidence angle can be of any value. Several spectrums can be measured at different incidence angles in order to obtain a fuller spectrum. We mark the ellipsometric spectrum $s(\theta,\lambda)=\{S_1(\theta,\lambda),S_2(\theta,\lambda)\}$.

Additionally, goniometric measurements (reflection coefficient as a function of the incident angle) can be added to the measurement used for characterisation, so as to determine the thickness of the various layers, for one or several wavelengths. These measurements alone are insufficient as we want to determine the complex refraction index over a spectral range from $\lambda_m$ to $\lambda_M$.

So as to simplify the presentation, we mark $\Psi$ a set of reflectometric and/or ellipsometric spectrums (and possibly goniometric spectrums for a few wavelengths).

Without omitting any generality, we describe, in this description, the operating mode of the methods of the prior art and of the invention only for the case of a single thin layer of material, created on a known substrate.

The thickness of this layer is marked $\epsilon$ and the complex refraction index of the material with the wavelength $\lambda$ is marked n*($\lambda$).

In this regard, remember that the real (respectively imaginary) part of this complex refraction index is marked n($\lambda$) (respectively k($\lambda$)) and called "refraction index" (respectively extinction coefficient").

Additionally, we mark an error function $Er(\Psi^{(1)}, \Psi^{(2)})$—for example the average quadratic gap—between two spectrums $\Psi^{(1)}$ and $\Psi^{(2)}$.

For example, we can take, when there are ellipsometric spectrums over several angles $\theta_i$, i$\in$ {1 . . . n}, and a reflectometric spectrum:

$$Er(\Psi^{(1)}, \Psi^{(2)}) = \frac{1}{\lambda_M - \lambda_m} \int_{\lambda_m}^{\lambda_M} \left[ \frac{1}{n} \sum_{i=1}^{n} [S_1^{(1)}(\theta_i, \lambda) - S_1^{(2)}(\theta_i, \lambda)]^2 + [S_2^{(1)}(\theta_i, \lambda) - S_2^{(2)}(\theta_i, \lambda)]^2 \right] + [R^{(1)}(\lambda) - R^{(2)}(\lambda)]^2 \right] d\lambda \quad (1)$$

with $\Psi^{(1)}(\lambda)=\{S_1^{(1)}(\theta_i,\lambda),S_2^{(1)}(\theta_i,\lambda),R^{(1)}(\lambda)\}$
$\Psi^{(2)}(\lambda)=\{S_1^{(2)}(\theta_i,\lambda),S_2^{(2)}(\theta_i,\lambda),R^{(2)}(\lambda)\}$
and i$\in$ {1 . . . n}

Weighing factors can be introduced into the integral so that the error function can take into account the variations in the accuracy of the measurements of the spectrums.

The optical characterisation of layers of material is generally based around two applications.

The first application is the dimension control of the deposit of thin layers that are used in microelectronics.

Usually we know the deposited material, i.e. we know the complex refraction index of this material at the first wavelengths used for the characterisation.

The laws applied by the complex refraction index are either tabulated or approximated by known physical laws such as, for example, the Cauchy model, the Sellmeier model (see document [3]), the Forouhi laws (see document [4]), and the harmonic oscillator laws (see document [5]). These laws are defined by a finite number of parameters.

For example, a Cauchy type law without absorption, is with two parameters, is defined in the following manner:

$$\text{Re}[n*(\lambda)] = n(\lambda) = a_0 + \frac{a_1}{\lambda^2}$$

$$\text{Im}[n*(\lambda)] = k(\lambda) = 0$$

When we are certain of the value of the coefficients $a_i$ (i$\in$ {0,1}) but we do not know the thickness, a search algorithm is used in order to find the thickness which minimises the error between the measurement Ψ and the theoretical result Ψ̄ taking into consideration the modelled index.

The search algorithm can be, for example, the Simplex method, the Tabou search, the Levendt-Marquart method or the simulated annealing method (see chapter 10 in document [6]).

When the refraction index is approximate, the coefficients $a_i$ are integrated into the adjustment process of Ψ and Ψ̄. The search for the coefficients $a_i$ constitutes a method of characterising the refraction index.

However, when the law applied by this refraction index is unknown (it happens that the material is unknown or that it is poorly described by known physical laws), this method remains approximate and the thickness risks being erroneous.

The second application is the characterisation of materials.

The employed method remains unchanged, except that the material is not really known. It is precisely the complex refraction index function that is the closest to reality that is targeted.

The type of law can be chosen via analogy with other materials. However, the law applied by the complex refraction index can be complicated, which is for example the case of a harmonic oscillator law.

$$[n(E) + jk(E)]^2 = 1 + \sum_{i=1}^{n} \frac{A_i}{E + E_i + j\Gamma_i} - \frac{A_i}{E - E_i + j\Gamma_i}$$

In the above expression, $j^2 = -1$ and the refraction index and the extinction coefficient are expressed as a function of E and not of λ, with $E = 1240/\lambda$ (λ in nm).

In this case, the coefficients of the oscillators are difficult to find if we do not know their value range. The search is difficult to automate, as the search algorithms can give erroneous results and the time wasted can be substantial.

There is an alternative to the search for coefficients: the point to point method (PAP). This PAP method proposes not to choose a physical law and to search the complex refraction index of the material for each wavelength $\lambda_i$, where i∈ [1 ... n], with $\lambda_1 = \lambda_m$ and $\lambda_n = \lambda_M$.

For each $\lambda_i$, a search algorithm tries to find the thickness, the index $n(\lambda_i)$ and the extinction coefficient $k(\lambda_i)$ which minimise the error between the measured values $\Psi(\lambda_i)$ and the theoretical result Ψ̄ $(\lambda_i, n(\lambda_i), k(\lambda_i), \epsilon)$.

Such a method poses a problem because the different points $(\lambda_i, \epsilon, n(\lambda_i), k(\lambda_i))$ are not necessarily physically compatible among themselves: for example, the found thickness can vary depending on the wavelength and the law applied by the complex refraction index, more simply called the index law, can have discontinuities.

This method is usually only valid when the thickness is fully known and that the measurements are of good quality.

PRESENTATION OF THE INVENTION

The purpose of the invention is to resolve the previous inconveniences.

The method which is the object of the invention allows to characterise a material without using a physical model, i.e. without using a physical law applied by the complex refraction index of the material under scrutiny. It is therefore especially useful when such a law is unknown.

This method constitutes an alternative to the aforementioned known methods of characterisation. It can be called "method of nodes" as it uses "nodes", i.e. points having coordinates $(\lambda_i, n^*_i)$, where $n^*_i$ is the value taken by the complex refraction index with the wavelength $\lambda_i$ and i takes a limited number of values (whole numbers).

Precisely, the purpose of the invention is a method for optical characterisation of at least one layer of material in an interval A of values taken by a function α of an optical wavelength λ, when λ varies in an interval of wavelengths, this layer being created on a substrate, this method being characterised in that it comprises the following stages:

1) we carry out a group of reflectometry and/or ellipsometry measurements over the interval A, this set of measurements leading to a measured spectrum, marked Ψ, and we choose the methods for calculating associated with the nature of the measurements and with the type of layer to be characterised;

2) we choose m initial values $\alpha_1 \ldots \alpha_m$ of the function α, belonging to this interval A, m being a whole number at least equal to 1, and we define an interval B as being the set of points α of the interval ranging from the smallest to the biggest number among $\alpha_1 \ldots \alpha_m$, when m is greater than 1, and as being the interval A when m equals 1;

3) we choose m complex initial values of a complex refraction index $n^* = n + jk$ for the m points $\alpha_i$, i ranging from 1 to m;

4) when m is not 1, we choose an interpolation law which allows to calculate the refraction index $n(\alpha)$ of the material over the interval B, from the points $(\alpha_i, n_i)$, with $n_i = n(\alpha_i)$, i ranging from 1 to m, and when m equals 1, $n(\alpha)$ is taken equal to the number $n_1(\alpha_1)$ over the entire interval B;

5) we choose M variable parameters, M being less than or equal to 2 m+1;

6) we choose an error function Er(Ψ, Ψ̄) which characterises the difference between a measured spectrum Ψ and a theoretical spectrum Ψ̄;

7) using a minimizing function of Er(Ψ, Ψ̄) with M parameters, we perform the following series of stages:

a) by applying the interpolation law of $(\alpha_i, n_i)$ is over the interval B, we deduce $n(\alpha)$, α belonging to B;

b) by using $n(\alpha)$ and the thickness ε of the layer, and methods for calculating spectrums, we calculate a theoretical spectrum Ψ̄ $(n(\alpha), \epsilon)$;

c) we compare Ψ and Ψ̄ by using Er(Ψ, Ψ̄) and, if Er(Ψ, Ψ̄) is sufficiently small, i.e. less than a predetermined value e, or is minimal, we go to stage e), otherwise we go to stage d);

d) we make the M variable parameters vary so as to tend to the minimum of Er (Ψ, Ψ̄), and we return to stage a);

e) if Er(Ψ, Ψ̄) is less than e, we then obtain a set of M variable parameters, for which Er(Ψ, Ψ̄(n(α,M),ε)) is minimal and the refraction index is then taken equal to the last one obtained, and if Er (Ψ, Ψ̄) is greater or equal to e we go to stage 8).

8) we increase the number m of initial values of the function α and we return to stage 2).

It is therefore, for example, possible to perform optical characterisation:

over an interval of wavelengths λ, in this case the interval [λmin, λmax], or over an interval of inverse wavelengths 1/λ, in this case over an interval [(1/λ)min, (1/λ)max], where (1/λ)min is equal to 1/(λmax) and (1/λ)max is equal to 1/(λmin);

or over an interval of energies E (with $E = h\nu = hc/\lambda$ where h is the Planck's constant, c the speed of the light in the vacuum and ν the frequency corresponding to (λ), in this case over an interval [E min, E max], where E min is equal to hc/(λmax) and E max is equal to hc/(λmin); or, more generally, over an interval [αmin, αmax] of values taken by a function α of the variable λ.

Furthermore, it is appropriate to note that the invention can be used to characterise a spectrum or a part of a spectrum.

Each interpolation law can be chosen from among the linear interpolation laws, the cubic interpolation laws, the polynomial interpolation laws and the interpolation laws for example of "spline" function type.

According to a preferred embodiment of the method which is the object of the invention, the spectrum is evenly sampled in α (λ), meaning that the initial values of the function α (see the aforementioned stage 2) are evenly distributed over the interval A, the distribution of the nodes thus being homogenous.

As previously seen, α (λ) can be chosen from among λ, 1/λ and hc/λ or any other function of λ, where h is the Plank's constant and c is the speed of the light in the vacuum.

Preferably, in the aforementioned stage 6), we measure the error over an interest interval C which is included in the interval B or equal to this interval B.

The M variable parameters can be the real parts of the refraction indexes at points $α_i$, i ranging from 1 to m, or the imaginary parts of these refraction indexes, or these M variable parameters can be constituted by the thickness of the material for which we are searching the refraction index.

Another purpose of the invention is another method for optical characterisation of at least one layer of a material in an interval of wavelengths [λ min, λ max], this layer being created on a substrate, this other method being characterised in that:

we carry out a set of reflectometry and/or ellipsometry measurements, this set of measurements leading to a measured spectrum, marked Ψ;

we choose m initial wavelengths $λ_1 \ldots λ_m$ belonging to this interval, m being a whole number at least equal to 1, we associate a refraction index to each wavelength;

we choose an interpolation law at least for the refraction index of the material, for wavelengths lying between the initial wavelengths $λ_1 \ldots λ_m$;

we choose M initial parameters, M being at least equal to m, namaly an initial refraction index $n_i$ for each initial wavelength $λ_i$, $1≦i≦m$, the initial wavelengths being chosen so as to determine via interpolation at least the refraction index for any wavelength within the interval [λ min, λ max], the couples $(λ_i, n_i)$ being called nodes;

we choose reflectometry and ellipsometry methods of calculation;

we also choose an error function Er, representative of the difference between two spectrums $Ψ_1$ and $Ψ_2$, the spectrums $Ψ_1$ and $Ψ_2$ being calculated or measured over a number of points greater than the number m of nodes;

using the m initial wavelengths, the M initial parameters and the interpolation law, we implement the following optimisation process:

we determine a theoretical spectrum, marked $\overline{Ψ}$, depending on the chosen methods of calculation, and on the index deduced via interpolation of its value at $λ_i$, i ranging from 1 to m, over the spectrum [λmin, λmax];

we determine the error Er(Ψ, $\overline{Ψ}$), between the measured spectrum and the theoretical spectrum;

we minimise this error by varying the position of the values of the unknown indexes and/or the thickness of the layer and/or the values of the refraction indexes with initial wavelengths, and we obtain a spectrum;

we add other wavelengths to the initial wavelengths $λi \ldots λm$, the added wavelengths constituting new nodes;

we repeat the method by choosing a number m' of initial wavelengths, m' being greater than m, and M' initial parameters, M' being greater than M, until the accuracy of each spectrum thus best represented is equal to a predetermined accuracy.

In this case, according to a first specific embodiment, m is at least equal to 2; according to a second specific embodiment, m is equal to 1 and we choose equal initial refraction indexes.

Also in this case, according to a specific embodiment, the material is non absorbent and the number M is equal to m, the extinction coefficient of the material being set equal to 0; according to another specific embodiment, M is at least equal to 2 m, we furthermore choose an interpolation law for the extinction coefficient of the material, for each initial wavelength $λi$, $1≦i≦m$, furthermore we choose an initial extinction coefficient $k_i$, the initial wavelengths furthermore being chosen so as to be able to determine via interpolation the extinction coefficient for any wavelength of the interval [λ min, λ max], and within the optimisation process, we minimise the error by also varying the values of the extinction coefficients at the initial wavelengths and the added wavelengths are furthermore placed so as to best represent the spectrum of the extinction coefficient of the material.

In the case of this other specific embodiment, m can be equal to 1 and we can choose equal initial refraction indexes and equal initial extinction coefficients.

Still in the case of this other method which is an object of the invention, the layer of material can be thin, i.e. with a thickness less than the coherence length of the light used for measuring, we can choose an additional initial parameter, namely an initial layer thickness, and in the optimisation process we can minimise the error by also varying the value of the layer thickness; in an alternative, the layer of material can be thick, i.e. not thin, and M can be at most equal to 2 m; in another alternative, the thickness of the layer of material can be known with sufficient accuracy and M is at most equal to 2 m.

The distribution of the nodes can be homogenous.

BRIEF DESCRIPTION OF THE DRAWINGS

The invention will be better understood upon reading the description of the below embodiments, given by way of non-restrictive examples, making reference to the annexed drawings among which.

DETAILED DESCRIPTION OF PARTICULAR EMBODIMENTS

The invention proposes an alternative to the aforementioned standard methods. It allows to combine the coherence of a layer model (corresponding to a continuous index law and to constant physical thicknesses), with the generality concerning the index law to be found (as in the PAP method). Furthermore, the resolution is only limited by the resolution of the measured spectrum.

In the method according to the invention, the spectrum of index $n^*(\lambda)$ is characterised by:
- a limited number of "nodes" which are points having co-ordinates $(\lambda_i, n_i, k_i)$ or $(\lambda_i, n^*_i)$, with $n_i = n(\lambda_i)$, $k_i = k(\lambda_i)$ and $n^*_i = n_i + jk_i$, where $j^2 = -1$, and
- an interpolation law between the nodes, which can be, for example, linear, cubic, of "spline" type or polynomial (of any given degree).

This interpolation law allows to calculate, from the nodes, the refraction indexes and the extinction coefficients for the wavelengths located between the nodes.

For example, when the refraction index is characterised by a set of value for wavelengths $\lambda_1 \ldots \lambda_m$, we can use a linear interpolation between two wavelengths $\lambda_i$ and $\lambda_{i+1}$ to calculate the index n at the wavelength $\lambda$ (see document [6] chapter 3):

$$n(\lambda) = \frac{(\lambda_{i+1} - \lambda)n(\lambda_i) + (\lambda - \lambda_i)n(\lambda_{i+1})}{\lambda_{i+1} - \lambda_i}$$

with $\lambda_i < \lambda < \lambda_{i+1}$

We can do the same for the extinction coefficient.

When the number of nodes makes it possible, more complex interpolation formulae, bringing into play nearby nodes, can be used (see document [6] chapter 3).

A layer model is therefore characterised by a thickness $\epsilon$ and a family of nodes.

Hereafter we present an example of the method according to the invention. In this example, the measurements $\Psi$ are constituted of a reflectometry measurement $R(\lambda)$ and an ellipsometry measurement $S_{1,2}(\theta,\lambda)$ where $\theta$ is the incidence angle of the light beam that is transmitted onto the layer to be studied during measuring via ellipsometry.

This layer is a thin layer so that the thickness of this layer is also a variable of the problem. Moreover, we suppose that only one layer is unknown, this layer being created on a known substrate.

We will first of all briefly explain this example which uses an algorithm (algorithm of the "nodes method" according to the invention).

From assumed information about the thickness $\epsilon$ of the scrutinised layer and about the refraction index $n(\lambda)$ and about the extinction coefficient $k(\lambda)$ of the material of this layer, we create initial nodes (only a few) and an initial thickness $\epsilon$.

We thus have m nodes and, via interpolation, we can find $n(\lambda)$ and $k(\lambda)$ when $\lambda$ is different from the values of the wavelengths associated with the nodes.

From the initial thickness $\epsilon$ and these initial values $n(\lambda)$ and $k(\lambda)$, we determine the theoretical spectrum $\Psi$ by using ellipsometric and reflectometric calculations.

Furthermore, by means of ellipsometric and reflectometric devices and a spectrometer, we obtain $S_{1,2}(\theta,\lambda)$ and $R(\lambda)$ and we deduce the measurements marked $\bar{\Psi}$ (for measuring conditions $\theta$ and $\lambda$).

We then compare $\Psi$ and $\bar{\Psi}$ by using an error function Er and we optimise the refraction index value and the extinction coefficient value at the different nodes as well as the thickness value, by trying to minimise $Er(\Psi, \bar{\Psi})$.

Once these values have been optimised and if the accuracy on the spectrum $n(\lambda)$, the spectrum $k(\lambda)$ and the thickness $\epsilon$ is insufficient, we introduce new nodes, we make the thickness $\epsilon$ vary and we recommence the determination of $\Psi$, the comparison of $\Psi$ and $\bar{\Psi}$ and the optimisation that are aforementioned, etc.

We break the thus defined loop when the accuracy on each of the spectrums $n(\lambda)$ and $k(\lambda)$ and on the thickness $\epsilon$ is considered to be sufficient (satisfactory adjustment of $\Psi$ and $\bar{\Psi}$).

The spectrums $n(\lambda)$, $k(\lambda)$ and the thickness $\epsilon$ are thus characterised.

In a non-restrictive illustration we find a layer thickness $\epsilon$ equal to 212.3 nm.

Figure 1:
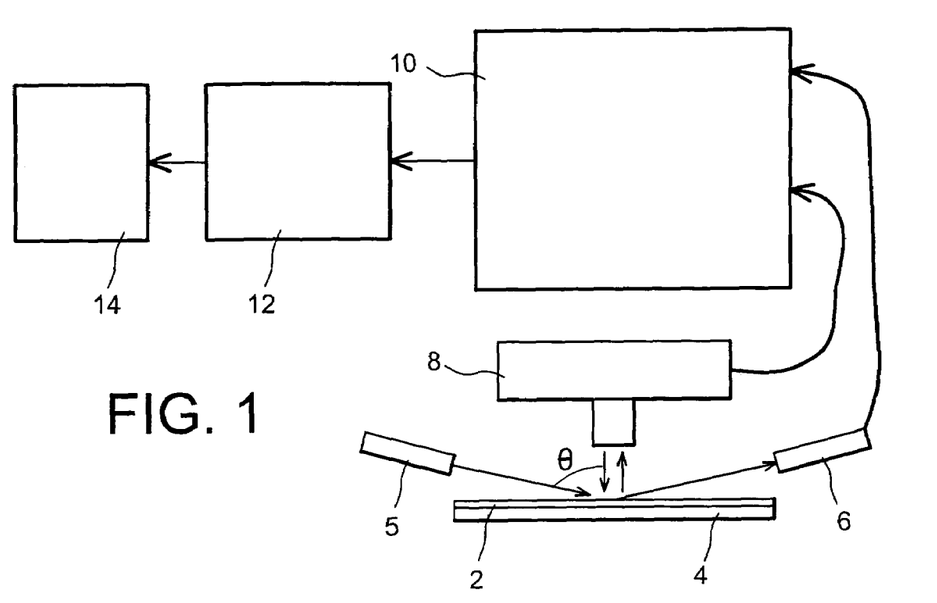
FIG. 1 is a diagrammatic view of devices allowing to characterise a layer according to the invention.

FIG. 1 diagrammatically shows the scrutinised layer 2, created on a substrate 4. We can see the ellipsometric device 5,6, the reflectometric device 8 and the spectrometer 10. Furthermore, we can see electronic processing means 12, comprising a computer and allowing to characterise $n(\lambda)$, $k(\lambda)$ and $\epsilon$ according to the information supplied by the spectrometer 10 and according to the method of the invention.

These means 12 are equipped with display means 14 which allow, in particular, to display the curve of the variation of n as a function of $\lambda$ and the curve of the variation of k as a function of $\lambda$.

We will now consider the illustration in greater detail.

Phase 1

The method of this example firstly comprises an initialisation stage.

The algorithm starts with a limited number of nodes, more precisely at least one node. We can therefore start with a single node, by imposing a refraction index and an extinction coefficient which remain constant when the wavelength varies.

We chose node positions so as to, from this node family, deduce the entire spectrum via interpolation. The layer model therefore has 3 parameters or more, as the thickness is also a variable to be determined. The index table over the entire spectrum is therefore deduced from the nodes via interpolation.

This is the case when the thickness of the layers is about the dimension of the wavelength (thin layers). But when the thickness of the layer is greater than the coherence length of the light source, the thickness barely enters into the calculation of the layer response, and is therefore no longer a variable of the problem.

For example, in the case of optical disks (CDROM), on which a very thick layer is deposited (a thickness of about 1 millimetre), the reflection coefficient of such a layer is no longer a function of the thickness of the layer but purely of the refraction index of the latter, the coherence length of the incident light beam being less than the thickness of the layer. In this precise case, the coherence length of the incident beam is determined by the roughness of the layers.

We choose, for example, to place the first two nodes at the ends $\lambda$ min and $\lambda$ max of the spectrum. The complex index values at these ends are chosen according to the type of material under scrutiny. For example, on an ellipsometric spectrum between 300 nm and 800 nm of a thin layer of photoresist, we take n(300 nm)=n(800 nm)=1.5 and k(300 nm)=k(800 nm)=0.

When the spectrum is only characterised by two nodes, the index between the ends is determined via linear interpolation. In the case under consideration, we therefore have $n(\lambda)=1.5$ and $k(\lambda)=0$ for belonging to [300 nm, 800 nm].

From three nodes up, we rather opt for cubic interpolation in order to obtain softer forms of index law compared to those obtained via linear interpolation.

The initial thickness is, itself, chosen as close as possible to the real thickness.

Phase 2

We then proceed with an optimal determination of the values of the refraction index and of the extinction coefficient on the nodes and of the thickness value.

To accomplish this, the spectrums $\overline{\Psi}(\lambda)$ are calculated by means of the used layer model, resulting from the choice of nodes, the interpolation law and the thickness of the layer.

The physical model used to calculate $\overline{\Psi}$ of course depends on the applied method for measuring, i.e. in particular on the incidence angle of the light, on the applied spectrum and on the model of thin layers or of thick layers if appropriate (see for example the model of stacked layers in document 3)).

The spectrums $\Psi$ being constituted of a set of measurements of diverse nature (for example ellipsometric and reflectometric measurements), we use a reflectometric (respectively ellipsometric) calculation method for reflectometric (respectively ellipsometric) measurements.

The reflectometric and ellipsometric measurements are combined by means of an error function $Er(\Psi, \overline{\Psi})$ which is for example of the type defined by the equation (1).

Thanks to a search function, we minimise the difference between $\overline{\Psi}(\lambda)$ and $\Psi(\lambda)$, by varying the value of the refraction index and the value of the extinction coefficient at the position of each of the nodes as well as the layer thickness (if this thickness is an important factor in the calculation of $\overline{\Psi}$). When the difference is minimal, that being when $Er(\Psi, \overline{\Psi})$ is minimal, this signifies that the reflectometric and ellipsometric measurements coincide to their best (for a given number of nodes).

At this stage we obtain, for a known number of nodes and a known spectral position for each of these nodes, the layer model (refraction index, extinction coefficient and thickness) which best corresponds to the real layer.

The validity of the found model is better ensured as the number of measurements increases. To obtain a large number of measurements we can for example use several incidence angles of the light $\theta_i$, $1 \leq i \leq I$, for the ellipsometric spectrums, carry out a reflectometric measurement and complementary goniometric measurements.

Phase 3

Then, we increase the number of nodes.

We add a finite number of nodes. In a first embodiment, the added nodes are positioned so as to best represent the spectrums $n(\lambda)$ and $k(\lambda)$. By way of example, we place these additional nodes at spots where the difference between $\Psi$ and $\overline{\Psi}$ is maximum or at spots where the nodes are the furthest apart. We then return to phase 2 as long as the accuracy on each of the spectrums $n(\lambda)$ and $k(\lambda)$ and on the thickness $\epsilon$ is insufficient, i.e. not equal to a predetermined accuracy.

In a second embodiment, we insert new nodes between two nodes of the set of previously chosen nodes, these new nodes being evenly distributed over the spectrum.

All the same it is appropriate to heed the following.

When we increase the number of nodes, the position of the old nodes does not need to be conserved. For example, assume that we evenly sample a spectrum from 400 nm to 800 nm with 3 nodes. These nodes are therefore respectively located at 400 nm, 600 nm and 800 nm. When we increase to 6 nodes, the three additional nodes cannot be placed so that the spectrum is evenly sampled if we conserve the position of the old nodes. The position of the 6 nodes can be defined, is we wish to have even sampling, by the values 400, 480, 560, 640, 720 and 800 nm. The old middle node at 600 nm therefore disappears. To calculate the index value at these positions from the old nodes we use interpolation.

In the following we provide two common examples of application of the invention. These examples implement two types of materials which apply different laws.

From ellipsometric and reflectometric measurements we propose to find the physical laws applied by these materials.

We proceed in the following manner.

A fictitious material is created, this material applying a known theoretical law (a Cauchy law or a harmonic oscillator law), with parameters that we arbitrarily set. The variations of the complex refraction index as a function of the wavelength are thus perfectly known.

Furthermore, we impose a thickness of 200.00 nm for the material, on a silicon substrate, this latter also being well known.

Fictitious measurements (ellipsometric measurements, reflectometric measurements) are calculated, then noise induced so as to introduce an apparatus defect.

It all takes place as if we had used real measurements taken on the material. But contrary to reality we fully know the complex refraction index as we set it just as we set the thickness of the layer of material.

Here we "blindly" test the method, that meaning we start with an erroneous thickness (220 nm) and false complex refraction indexes, as they are supposed to be unknown.

We apply the method according to the invention then we compare the complex refraction index found with the is theoretical complex refraction index. We precisely find the same laws, as well as the same layer thickness.

As a first example, take a material whose complex refraction index applies to a Cauchy law such as:

$$n(\lambda) = 1.5 + 0.1\frac{300^2}{\lambda^2} + 0.1\frac{300^4}{\lambda^4}$$

$$k(\lambda) = 0$$

This index law is typical of photoresists (in the spectral range from 300 nm to 800 nm).

In order to find, using the nodes method (i.e. the method according to the invention), the aforementioned index law, we carry out two measurements, namely an ellipsometric measurement at a 70° angle and a reflectometric measurement.

The processing conditions are as follows:
the processed spectrum lies between 300 nm and 800 nm;
at the start, the nodes are in the positions (300 nm, 1.6) and (800 nm, 1.6), this meaning that the index is considered as linearly varying between 300 nm and 800 nm, and that its value is constant (equal to 1.6);
the number of nodes is repeatedly increased according to the sequence 2→4→6;
during the node increasing procedure, the wavelength position of each node is calculated so that the sampling by $1/\lambda$ is regular ($\lambda$: wavelength), the density of points thus being increased around the low wavelengths;

the interpolation law is a cubic law, when the number of nodes is greater than 2, otherwise it is linear; and the applied minimisation algorithm is a Simplex type algorithm.

Figure 2:
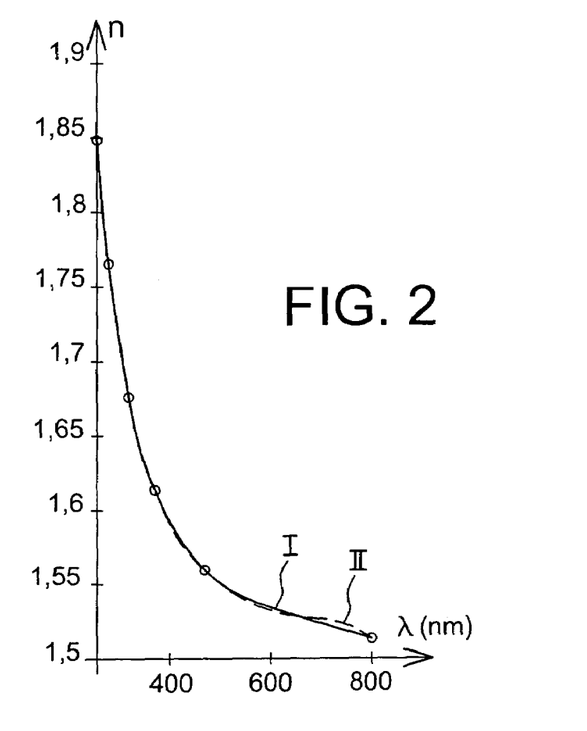
FIG. 2 shows the variations in the refraction index as a function of the wavelength, for a material obeying to a Cauchy law (curve I) and for a material characterised according to the invention (curve II)

FIG. 2 allows to compare the refraction index corresponding to the fictitious material which perfectly applies the Cauchy law (curve I) with the refraction index which we find via the nodes method (curve II), using 6 nodes (represented by circles in FIG. 2). We have used a $\Psi$ composed of an ellipsometric measurement $\{S_1(\lambda),S_2(\lambda)\}$ at 70° and a reflectometric measurement $R(\lambda)$.

We finally find a thickness of 199.8384 nm.

As for a second example, take a material whose complex refraction index applies a law with two harmonic oscillators, such as:

$$[n(E)+jk(E)]^2 = 1 + \sum_{i=1}^{2} \frac{A_i}{E+E_i+jG_i} - \frac{A_i}{E-E_i+jG_i}$$

with $j^2=-1$ and $E=1240/\lambda$ ($\lambda$ in nm)

$A_1=0.25\times1.5^2$ $A_2=0.25\times1.5^2$ $E_1=1240/400$ $E_2=1240/300$ $G_1=0.3$ $G_2=0.3$ In this second example, the nodes method is applied to a set of ellipsometric measurements carried out between 250 nm and 800 nm, at 75°, 70°, 60° and 45°, along with a reflectometric measurement. The real thickness of the material being 200 nm, we find a thickness of 200.25 nm with the nodes method. The adjustment to the index law considered in this second example is very good, as FIGS. 3A and 3B demonstrate.

Figure 3A:
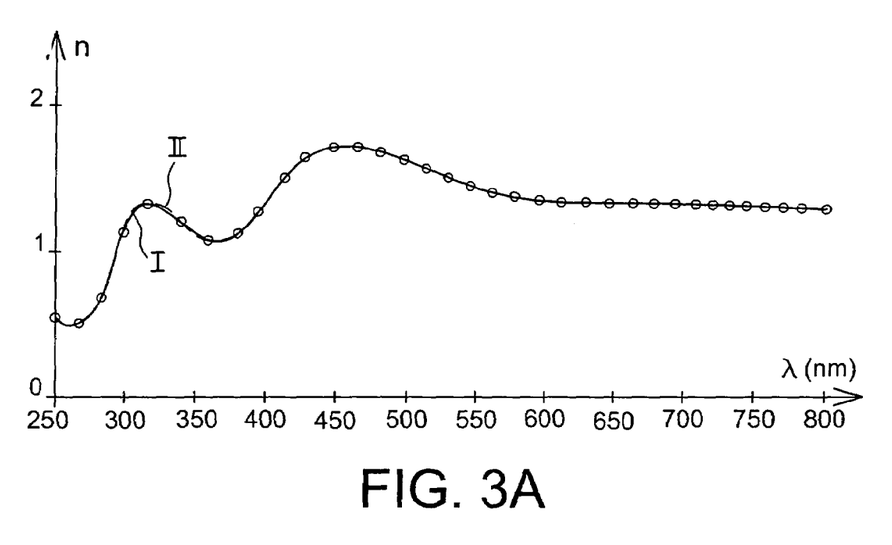
FIGS. 3A and 3B show the variations in the refraction index (respectively in the extinction coefficient) as a function of the wavelength, for a material obeying to a law with two harmonic oscillators (curve I) and for a material characterised according to the invention.
Figure 3B:
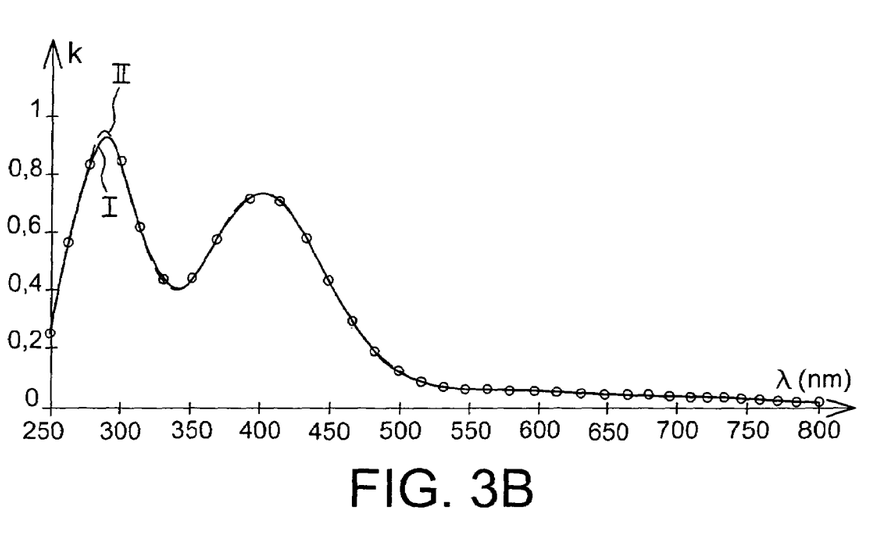

These FIGS. 3A and 3B respectively illustrate the reconstructions of the curves $n(\lambda)$ and $k(\lambda)$ of the material by means of the nodes method. The reconstruction is carried out using four ellipsometric spectrums and a reflectometric spectrum. The real absorption peaks are particularly well represented by the curve obtained via cubic interpolation between the nodes (represented by the circles in FIGS. 3A and 3B).

In FIG. 3A, the curve I (respectively II) corresponds to a refraction index n which perfectly applies the chosen law (respectively to a refraction index n found via the nodes method).

In FIG. 3B, the curve I (respectively II) corresponds to an extinction coefficient k which perfectly applies the chosen law (respectively to an extinction coefficient k found via the nodes method).

Examples of the invention have just been described above. More generally speaking, we note that in the invention we consider a set X of values, with $X=\{n_1,n_2,\ldots,n_i,\ldots n_m,k_1,k_2,\ldots k_i,\ldots k_m,\epsilon\}$, where $n_i$ is the value of the refraction index (real) corresponding to $\lambda_i$, $i\in\{1\ldots m\}$, m being the number of nodes $k_i$ is the value of the absorption coefficient at the node corresponding to $\lambda_i$, $i\in\{1\ldots m\}$, $\epsilon$ is the thickness of the scrutinised layer.

In this case, the operation for minimizing the error $Er(\Psi, \overline{\Psi})$ means finding the set or "vector" X such that Er is minimal.

When we do not assert any specific constraints, the minimizing is a minimizing with $2\times m+1$ parameters. We can of course introduce constraints in order to reduce the number of variables.

In particular, if we know that the material is non-absorbent, we impose $k_i=0$ for all i of $\{1\ldots m\}$ and X becomes: $X=\{n_1,n_2\ldots,n_i,\ldots n_m,\epsilon\}$.

If through a complementary measurement (for example a goniometric measurement or a non-optical direct measurement) we know with sufficient accuracy the thickness of the scrutinised layer, the thickness $\epsilon$ is no longer a variable and we obtain: $X=\{n_i, n_2\ldots,n_i,\ldots n_m, k_1, k_2,\ldots k_i, \ldots, k_m\}$.

Of course, the two previous options can be combined.

In the following we explain an embodiment of the invention in a more general form than the previous examples.

Given that $\alpha(\lambda)$ is a function of the wavelength $\lambda$ of the light used in the measurements, we can for example choose:

$\alpha(\lambda)=$(see FIGS. 3A and 3B where the spectrum is evenly sampled in $\lambda$)

$\alpha(\lambda)=1/\lambda$ (see FIG. 2 where the spectrum is evenly samples in $1/\lambda$)

$\alpha(\lambda)=hc/\lambda$ where h is the Planck's constant and c the speed of light in the vacuum, $\alpha(\lambda)$ then being homogenous with an energy.

Given that A is the interval of the spectrum of measurement, B is the spectral interval described by the "nodes" and C is the interval of interest.

The interval C is included in the interval B or equal to this interval B. Likewise, the interval B is included in the interval A or equal to this interval A.

Figure 4:
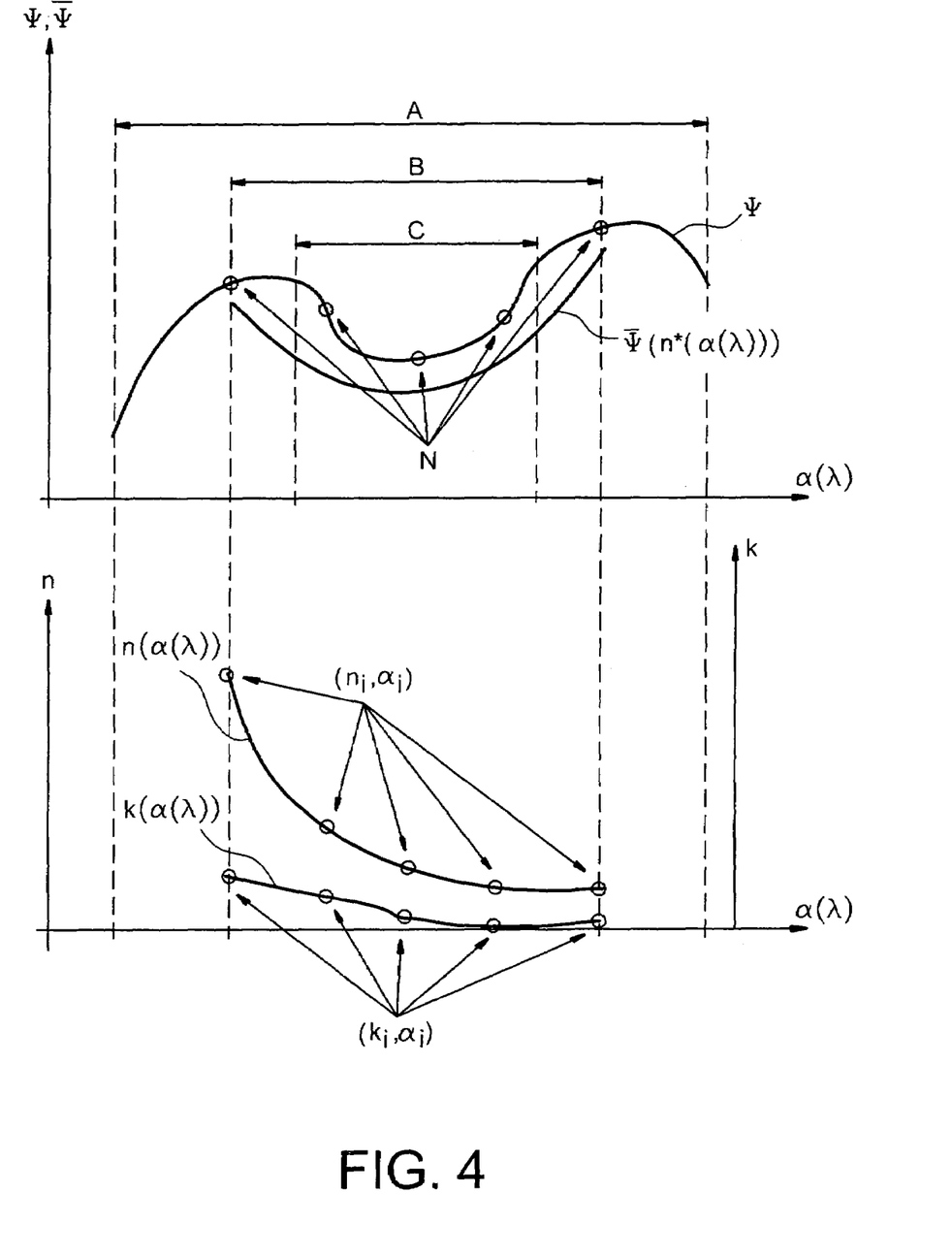
FIG. 4 diagrammatically illustrates the parameters used in a generalisation of examples of the invention.

We specify that each of the intervals A, B and C is of $[\alpha_m, \alpha_M]$ type where $\alpha_m$ is less than $\alpha_M$ and there are two wavelengths $\lambda_k$ and $\lambda_i$ such that $\alpha_m=\alpha(\lambda_k)$ and $\alpha_M=\alpha(\lambda_1)$. By way of non-restrictive illustration, FIG. 4 shows an example of the intervals A, B and C and of the variation curves of $\Psi$ and $\overline{\Psi}$ as a function of $\alpha(\lambda)$, $\overline{\Psi}$ in fact being a function of $n^*(\alpha(\lambda))$.

The circles N represent the nodes.

$n^*$ is the complex index which is expressed here as a function of $\alpha(\lambda)$ and whose real and imaginary parts are respectively marked $n(\alpha(\lambda))$ and $k(\alpha(\lambda))$.

We also see, by way of non-restrictive example, an example of the variations curve of n (respectively k) as a function of $\alpha(\lambda)$, passing through the points having co-ordinates $(n_i,\alpha_i)$ (respectively $(k_i, \alpha_i)$, where $\alpha_i=\alpha(\lambda_i)$, $n_i=n(\alpha_i)$, $k_i=k(\alpha_i)$, $1\leq i\leq m$ (m being a natural number other than zero).

In FIG. 4 we note the relation between the nodes N, the points $(n_i, \alpha_i)$ and the points $(k_i, \alpha_i)$.

In the embodiment under consideration, we use an algorithm comprising the following stages:

1. we carry out the measurements $\Psi$ over the interval A and we choose the calculation methods associated with the measurements (ellipsometric or reflectometric calculations);

2. we choose m numbers $\alpha_i$ (constituting m initial values of the function $\alpha$), i belonging to $\{1,\ldots m\}$, with $m\geq 1$, and $\{\alpha_i\}\subset A$ (the $\alpha_i$ corresponding to the "nodes"); when $m>1$, B is defined as the set of points $\alpha$ such that $\min(\alpha_i)\leq\alpha\leq\max(\alpha_i)$; when $m=1$, we have $B=A$;

3. we choose m initial values of complex index $n^*$ at the m points $\alpha_i$, i belonging to $\{1,\ldots m\}$;

4. if $m\neq 1$ we choose an interpolation law which allows to calculate the refraction index $n(a)$ over the interval B from the points $(\alpha_i, n_i)$, i belonging to $\{1,\ldots,m\}$; if $m=1$, then $n(\alpha)=n_1(\alpha_1)$ over the entire interval B;

5. we choose M variable parameters with $M \leq 2m+1$; these parameters can be for example:

the real parts of the refraction indexes at points $\alpha_i$, i belonging to $\{1, \ldots, m\}$, or the imaginary parts of the refraction indexes at these same points, or the thickness of the material for which we are searching the refraction index;

6. we choose an error function $Er(\Psi, \overline{\Psi})$ which characterises the difference between a measured spectrum and a theoretical spectrum; generally, the error is measured over the interval C;

7. using a minimizing function of $Er(\Psi, \overline{\Psi})$ with M parameters, we perform the following series of stages:

a) by applying the interpolation function of $(\alpha_i, n_i)$ over B, we deduce $n(\alpha)$ with $\alpha$ belonging to B;

b) by using $n(\alpha)$ and the thickness $\epsilon$ and methods for calculating spectrums, we calculate the theoretical spectrum $\overline{\Psi}(n(\alpha), \epsilon)$;

c) we compare $\Psi$ and $\overline{\Psi}$ by using $Er=Er(\Psi, \overline{\Psi})$; if Er is sufficiently small (i.e. if Er is less than a predetermined value $\underline{e}$), or if Er is minimal, we go to stage e), otherwise we go to stage d);

d) we make the M variable parameters vary so as to tend to the minimum of Er and we return to stage a);

e) if Er is less than $\underline{e}$ we then obtain a set of M parameters such that $Er(\Psi, \overline{\Psi}(n(\alpha,M),\epsilon))$ is minimal and the refraction index calculation is completed: this index is taken equal to the last one obtained; and if Er is greater than or equal to $\underline{e}$ we go to stage 8).

8. We increase m and we return to stage 2).

It is appropriate to note that the invention can not only use wavelength ($\lambda$) samplings but also frequency ($c/\lambda$ or simply $1/\lambda$) samplings, energy ($hc/\lambda$) samplings and, more generally, samplings with parameters which are functions of the wavelength.

Furthermore, it is appropriate to note that an aforementioned essential stage of the algorithm (stage 8) is not restricted to adding a set of nodes to the already existing nodes: it encompasses the more general case where the number of nodes increases. This means, in a specific embodiment of the invention, that after minimizing with 3 nodes, if we want to increase to 6 nodes in all, the position of the 3 old nodes is "erased" so as, for example, to have a constant density of nodes over the spectrum. In practice, this is the best option. The information about the position of the old nodes is not lost as the index value at the old nodes is used to calculate the values of the 6 new nodes (in fact 3 new nodes plus 3 old nodes).

Thus, according to a specific embodiment of the method according to the invention, we can increase the number of initial values of the function $\alpha$ by adding one or several values to the extant initial values; however, according to a preferred embodiment, we can increase the number of initial values of the function $\alpha$ by replacing the extant initial values with new initial values whose number is greater than the number of extant initial values.

The invention in not restricted to the characterisation of thin layers. It also applies to the characterisation of thick layers.

Furthermore, the invention is not restricted to the characterisation of a single layer, created on a substrate. It also applies to the characterisation of two, or more than two, layers created on a substrate.

The following documents were cited in the description:

[1] R. M. A. Azzam and N. M. Bashara, Ellipsometry and Polarised Light, North-Holland Physics Publishing, 1997, chapter 6.

[2] B. K. Minhas, S. A. Coulombe, S. Sohail, H. Naqvi and J. R. McNeill, Ellipsometry scatterometry for the metrology of sub-0.1-µm-linewidth structures, Applied Optics, 37(22): 5112-5115, 1998.

[3] M. Born and E. Wolf, Principle of Optics, Cambridge University Press Edition.

[4] A. R. Forouhi and I. Bloomer, Optical dispersion relations for amorphous semiconductors and amorphous dielectrics, Physical Review B, 34(10): 7018-7026, November 1986.

[5] F. L. Terry, Jr., A modified harmonic oscillator approximation scheme for the dielectric constants of $Al_xGa_{1-x}As$, Journal of Applied Physics, 70(1), 1991, pages 409-417.

[6] W. H. Press, S. A. Teukolsky, W. T. Vetterling and B. P. Flannery, Numerical Recipes in C, Cambridge University Press, 1992, chapters 3 and 10.

The invention claimed is:

1. A method for optical characterization of at least one layer of material in an interval A of values taken by a function $\alpha$ of an optical wavelength $\lambda$, when $\lambda$ varies in an interval of wavelengths, the at least one layer being created on a substrate, the method comprising:

1) carrying out a set of reflectometry and/or ellipsometry measurements over the interval A with ellipsometric and/or reflectometric devices and a spectrometer, the set of measurements leading to a measured spectrum, marked $\psi$, and choosing methods for calculating associated with a nature of the measurements and with a type of layer to be characterized;

2) choosing m initial values $\alpha_1 \ldots \alpha_m$ of the function $\alpha$, belonging to the interval A, m being a whole number at least equal to 1, and defining an interval B as being the set of points $\alpha$ of the interval ranging from the smallest to the biggest number among $\alpha_1 \ldots, \alpha_m$, when m is greater than 1, and as being the interval A when m equals 1;

3) choosing m complex initial values of a complex refraction index $n^*=n+jk$ for the m points $\alpha_i$, i ranging from 1 to m;

4) when m is not 1, choosing an interpolation law that allows calculating the refraction index $n(\alpha)$ of the material over the interval B, from the points $(\alpha_i, n_i)$, with $n_i=n(\alpha_i)$, i ranging from 1 to m, and when m equals 1, $n(\alpha)$ is taken equal to the number $n1(\alpha 1)$ over the entire interval B;

5) choosing M variable parameters, M being less than or equal to $2m+1$;

6) choosing an error function $Er(\psi, \overline{\psi})$ that characterizes the difference between a measured spectrum $\psi$ and a theoretical spectrum $\overline{\psi}$;

7) using a minimizing function of $Er(\psi, \overline{\psi})$ with M parameter, performing:

a) by applying the interpolation law of $(\alpha_i, n_i)$ over the interval B, deducing $n(\alpha)$, $\alpha$ belonging to B;

b) by using $n(\alpha)$ and the thickness $\epsilon$ of the layer, and methods for calculating spectrums, calculating a theoretical spectrum $\overline{\psi}(n(\alpha),\epsilon)$;

c) comparing $\psi$ and $\overline{\psi}$ by using $Er(\psi, \overline{\psi})$ and, if $Er(\psi, \overline{\psi})$ is less than a predetermined value $\underline{e}$, or is minimal, going to sub-step e), otherwise going to sub-step d);

d) making the M variable parameters vary so as to tend to the minimum of $Er(\psi, \overline{\psi})$, and returning to substep a);

e) if $Er(\psi, \overline{\psi})$ is less than e, then obtaining a set of M variable parameters, for which $Er(\psi, \overline{\psi}(n(\alpha,M),\epsilon))$ is minimal and the refraction index is then taken equal to the last one obtained, and if $Er(\psi, \overline{\psi})$ is greater or equal to e going to step 8);

8) increasing the number m of initial values of the function α and returning to step 2).

2. A method according to claim 1, further comprises increasing the number of initial values of the function a by adding one or plural values to extant initial values.

3. A method according to claim 2, further comprising increasing the number of initial values of the function a by replacing the extant initial values with new initial values whose number is greater than the number of extant initial values.

4. A method according to claim 2, wherein each interpolation law is chosen from among linear interpolation laws, cubic interpolation laws, polynomial interpolation laws, and interpolation laws of spline function type.

5. A method according to claim 1, wherein the initial values of the function a are evenly distributed over the interval A, the distribution of the nodes thus being homogenous.

6. A method according to claim 1, wherein $\alpha(\lambda)$ is chosen among $\lambda$, $1/\lambda$ and $hc/\lambda$, where h is the Planck's constant and c the speed of light in vacuum.

7. A method according to claim 1, further comprising measuring the error, at 6), over an interest interval C which is included in the interval B or equal to the interval B.

8. A method according to claim 1, wherein the M variable parameters are real parts of the refraction indexes at points $\alpha_i$, i ranging from 1 to m.

9. A method according to claim 1, wherein the M variable parameters are imaginary parts of the refraction indexes at points $\alpha_i$, i ranging from 1 to m.

10. A method according to claim 1, wherein the M variable parameters are constituted by the thickness of the material for which the refraction index is searched.

11. A method for optical characterization of at least one layer of a material in an interval of wavelengths [λ min, λ max], the at least one layer being created on a substrate, the method comprising:

carrying out a set of reflectometry and/or ellipsometry measurements with ellipsometric and/or reflectometric devices and a spectrometer, the set of measurements leading to a measured spectrum, marked ψ;

choosing m initial wavelengths $\lambda_1 \ldots \lambda_m$ belonging to the interval, m being a whole number at least equal to 1, and associating a refraction index to each wavelength;

choosing an interpolation law at least for the refraction index of the material, for wavelengths lying between the initial wavelengths $\lambda_1 \ldots \lambda_m$;

choosing M initial parameters, M being at least equal to m, an initial refraction index $n_i$, for each initial wavelength $\lambda_i$, $1 \leq i \leq m$, the initial wavelengths being chosen so as to determine via interpolation at least the refraction index for any wavelength within the interval [λmin, λmax], couples $(\lambda_i, n_i)$ being nodes;

choosing reflectometry and ellipsometry methods of calculation;

choosing an error function Er, representative of the difference between two spectrums $\psi_1$ and $\psi_2$, the spectrums $\psi_1$ and $\psi_2$ being calculated or measured over a number of points greater than the number m of nodes;

using the m initial wavelengths, the M initial parameters, and the interpolation law, implementing an optimization process of:

determining a theoretical spectrum, marked $\overline{\psi}$, depending on the chosen methods of calculation, and on the index deduced via interpolation of its value at $\lambda_i$, i ranging from 1 to m, over the spectrum [λmin, λmax];

determining the error Er $(\psi, \overline{\psi})$, between the measured spectrum and the theoretical spectrum;

minimizing the error by varying the position of the values of the unknown indexes and/or the thickness of the layer and/or the values of the refraction indexes with initial wavelengths, and obtaining a spectrum;

adding other wavelengths to the initial wavelengths $\lambda_i \ldots \lambda_m$, the added wavelengths constituting new nodes;

repeating the method by choosing a number m' of initial wavelengths, m' being greater than m, and M' initial parameters, M' being greater than M, until the accuracy of each spectrum thus best represented is equal to a predetermined accuracy.

12. A method according to claim 11, wherein m is at least equal to 2.

13. A method according to claim 11, wherein m is at least equal to 1 and equal initial refraction indexes are chosen.

14. A method according to claim 11, wherein the material is non absorbent and the number M is equal to m, the extinction coefficient of the material being set equal to 0.

15. A method according to claim 11, wherein:

M is at least equal to 2 m;

the method further comprising:

choosing an interpolation law for the extinction coefficient of the material;

each initial wavelength $\lambda_i$, $1 \leq i \leq m$ choosing an initial extinction coefficient $k_i$, the initial wavelengths furthermore being chosen so as to be able to determine via interpolation the extinction coefficient for any wavelength of interval [λ min, λ max];

within the optimization process, minimizing the error by also varying values of the extinction coefficients at the initial wavelengths, and further placing the added wavelengths so as to best represent the spectrum of the extinction coefficient of the material.

16. A method according to claim 15, wherein m is equal to 1 and equal initial refraction indexes and equal initial extinction coefficients are chosen.

17. A method according to claim 11, wherein the layer of material has a thickness less than coherence length of light used for measuring, and further comprising choosing an additional initial parameter of an initial layer thickness, and in the optimization process the error is minimized by also varying the value of the layer thickness.

18. A method according to claim 11, wherein the layer of material is thick, and M is at most equal to 2 m.

19. A method according to claim 11, wherein the thickness of the layer of material is known with a predetermined accuracy and M is at most equal to 2 m.

20. A method according to claim 11, wherein each interpolation law is chosen from among linear interpolation laws, cubic interpolation laws, polynomial interpolation laws, and interpolation laws for example of spline function type.

21. A method according to claim 11, wherein a distribution of the nodes is homogenous.

* * * * *